United States Patent [19]

Baker

[11] Patent Number: 5,475,134

[45] Date of Patent: Dec. 12, 1995

[54] PROCESS FOR MAKING SULFONATED FATTY ACID ALKYL ESTER SURFACTANT

[75] Inventor: Keith H. Baker, Cincinnati, Ohio

[73] Assignee: The Procter & Gamble Co., Cincinnati, Ohio

[21] Appl. No.: 167,682

[22] Filed: Dec. 16, 1993

[51] Int. Cl.⁶ .................................................. C07C 309/04
[52] U.S. Cl. ........................ 560/147; 252/549; 252/550; 252/551; 252/552; 252/554; 558/60
[58] Field of Search .................................. 252/549, 550, 252/121, 554, 552, 551; 558/60; 560/147, 149, 150

[56] References Cited

U.S. PATENT DOCUMENTS

| | | | |
|---|---|---|---|
| 3,954,643 | 5/1976 | Krings et al. | 252/96 |
| 4,253,993 | 3/1981 | Ramsey, III et al. | 252/548 |
| 4,404,143 | 9/1983 | Sekiguchi et al. | 260/400 |
| 4,416,809 | 11/1983 | Magari et al. | 252/557 |

FOREIGN PATENT DOCUMENTS

| | | |
|---|---|---|
| 3444198 | 6/1985 | Germany. |
| 3535184 | 4/1986 | Germany. |
| 4035935A1 | 5/1992 | Germany. |
| 57-180699 | 11/1982 | Japan. |
| 59-105099 | 6/1984 | Japan. |
| 60-88100 | 5/1985 | Japan. |
| 60-133095 | 7/1985 | Japan. |
| 61-9499 | 1/1986 | Japan. |
| 62-43499 | 2/1987 | Japan. |

OTHER PUBLICATIONS

Chemical Abstract, "Production of alpha–Sulfofatty Acid Ester Salt" JP890113423, May 1, 1989 and JP2290842, Nov. 30, 1990.

W. Stein and H. Baumann, "α–Sulfonated Fatty Acids and Esters: Manufacturing Process, Properties, and Applications"m Apr. 1974, pp. 323–329.

*Primary Examiner*—Richard L. Raymond
*Attorney, Agent, or Firm*—Jacobus C. Rasser; Jerry J. Yetter; Michael D. Jones

[57] ABSTRACT

An improved process for the production of sulfonated fatty acid alkyl ester surfactants containing low levels of impurities including disalt and dimethyl sulfate (DMS) impurities, said process comprising sulfonating fatty acid alkyl esters, forming a substantially anhydrous alkoxide solution, over-neutralizing to a pH of at least about 10 with the alkoxide solution, and re-neutralizing to a pH of about 5 to about 9. The substantially anhydrous alkoxide solution is formed by combining an alkoxide solution containing an alkoxide of the formula $(RO^-)_n M^{n+}$, a $C_1$ to $C_8$ alcohol, and no more than 1% by weight water with a sacrificial ester of the formula $R^1 COOR^2$, wherein the molar ratio of the sacrificial ester to water is from about 0.5:1 to about 2:1.

10 Claims, No Drawings

PROCESS FOR MAKING SULFONATED FATTY ACID ALKYL ESTER SURFACTANT

TECHNICAL FIELD

This invention relates to a process for preparing high purity sulfonated fatty acid alkyl ester surfactants. The process comprises a neutralization step wherein a sulfonated fatty acid alkyl ester acid mix is neutralized with an alkoxide solution that is substantially anhydrous. The alkoxide solution is prepared by combining an alkoxide solution containing no more than about 1% water and a sacrificial ester to eliminate water from the resulting solution. Preferably, the surfactants are subjected to a separate color improvement process prior to use in detergent compositions including laundry detergent compositions.

BACKGROUND OF THE INVENTION

Sulfonated fatty acid alkyl ester surfactants (alternatively referred to as α-sulfo fatty acid alkyl ester surfactants, alkyl ester sulfonate surfactants, etc.) are well-known in the detergent field and have been disclosed in, e.g., U.S. Pat. Nos. 5,118,440 (Cutler et al) and 4,438,025 (Satsuki et al), Japanese Laid Open Patent Publication Number 60-133097 (Application No. Showa 58-240021), Japanese Laid Open Patent Publication Number Sho 63-12466 (Patent Application No. Sho 61-151030), Japanese Laid Open Patent Publication Number Sho 59-105099 (Patent Application No.: Sho 57-215962), Japanese Laid Open Patent Publication Hei 2-173196 (Patent Application No. Sho 63-330479), Japanese Laid Open Patent Publication Number Sho 62-43500 (Patent Application No.: Sho 60-183729), and Japanese Laid Open Patent Publication Number Sho 50-151905 (Patent Application No.: 49-60284). Several processes for the manufacture of these sulfonated fatty acid alkyl ester surfactants have been disclosed in, e.g., U.S. Pat. Nos. 4,695,409 (Piorr et al) and 4,820,451 (Piorr et al), German Patent Application 3 535 184 (Imamura et al), Japanese Laid Open Patent Publication Number 290842/90 (Application Number 113423/89), and "The Journal of the American Oil Chemists Society", Vol. 52 (1975), pp. 323–329.

The processes for making the sulfonated fatty acid alkyl ester surfactants described in the technical literature, though, disclose the practicability and desirability of performing the neutralization step in aqueous media. The art has recognized certain problems inherent to such process steps, particularly handling difficulties and hydrolysis reactions. Certain of the processes yield undesirable levels of impurities such as sulfonated fatty acid salts (disalt), thereby producing a low-purity sulfonated fatty acid alkyl ester surfactant. These impurities deteriorate the desirable cleaning and viscosity characteristics of the sulfonated fatty acid alkyl ester surfactant.

Other processes described in the technical literature have observed the desirability of performing the neutralization of sulfonated fatty acid alkyl ester acid mix in a substantially anhydrous, lower alcohol solvent medium. See, e.g., Japanese Patent OPI Publication 90-290842. Unlike processes performed in aqueous media, processes performed under substantially anhydrous neutralization conditions result in a highly undesirable impurity, dimethyl sulfate (DMS). This impurity can be minimized by over-neutralizing an alkyl ester sulfonate acid mix to a pH of at least 10. However, at this higher pH range alkyl ester sulfonates readily react with water to convert to another highly undesirable impurity, sulfonated fatty acid salts (disalt).

Now, however, a process for making a sulfonated fatty acid alkyl ester surfactant having low levels of undesirable impurities has been discovered. By conducting the neutralization process step in accordance with the invention herein, in substantially anhydrous media with a substantially anhydrous alkoxide solution formed by combining an alkoxide solution containing a low level of water and a sacrificial ester, the resultant product has a lower level of disalt and DMS impurities. The reaction mixtures exhibit good handling and in-process flow properties. Therefore, it is an object of this invention to provide a process for making sulfonated fatty acid alkyl ester surfactants containing minimal amounts of undesirable impurities. It is a further object of this invention to provide high purity sulfonated fatty acid alkyl ester surfactants having good flow properties during processing and which, following a separate color improvement process, are useful in detergent products.

SUMMARY OF THE INVENTION

The present invention encompasses a novel process for preparing a sulfonated fatty acid alkyl ester surfactant, said process comprising:

A. sulfonating fatty acid alkyl esters;

B. combining an alkoxide solution containing no more than about 1% by weight water with a sacrificial ester of the formula $R^1COOR^2$ wherein $R^1$ is a $C_1$ to $C_4$ alkyl or benzoate and $R^2$ is a $C_1$ to $C_8$ alkyl to form a substantially anhydrous alkoxide solution; wherein the molar ratio of sacrificial ester to water is from about 0.5:1 to about 2.0:1;

C. over-neutralizing the product of step A to a pH of at least about 10 with the substantially anhydrous alkoxide solution of step B; and D. re-neutralizing the product of step C in a substantially anhydrous medium to a pH of about 5 to 9.

The resultant product solution of the novel process herein may be used directly in formulating detergent products, but is preferably subjected to a working-up procedure wherein the dark-colored impurities formed during sulfonation of the fatty acid alkyl esters are separated from the resultant solution and, subsequently, the surfactant is recovered from the solution. The resultant surfactant is useful in detergent compositions.

DETAILED DESCRIPTION OF THE INVENTION

Sulfonated fatty acid alkyl ester surfactants ("alkyl ester surfactants") are well-known in the art and are disclosed in the technical literature. These surfactants, when prepared according to the process of the present invention, comprise sulfonated fatty acid alkyl esters of the formula:

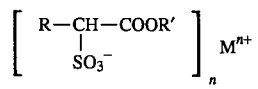

wherein R is on the average a $C_4$ to $C_{22}$ alkyl, R' is on the average a $C_1$ to $C_8$ alkyl, M is an alkali metal or alkaline earth metal cation, or a mixture thereof, and n is 1 when M is an alkali metal cation and n is 2 when M is an alkaline earth metal cation.

The sulfonated fatty acid alkyl esters ("alkyl esters sulfonates" or "sulfonated alkyl esters") constitute a major portion of the surfactant. Preferably, the sulfonated alkyl esters amount to about 80% to 100%, preferably about 90% to 100%, by weight of the surfactant. The alkyl ester surfactant will likely also contain certain impurities including sulfonated fatty acid salts, fatty acid alkyl esters, and organic and inorganic sulfate salts at levels of 0 to about 20%.

The hydrophobic portion of these sulfonated alkyl esters have the sulfonate group at the α position, i.e., the sulfonate group is positioned at the carbon atom adjacent the carbonyl group. The alkyl portion of the hydrophobic portion, which corresponds to the R portion of the sulfonated fatty acid alkyl esters, is on the average a $C_4$ to $C_{22}$ alkyl. Preferably, the alkyl portion of this hydrophobic portion, R, is on the average a saturated straight-chain $C_{10}$ to $C_{16}$ hydrocarbon, particularly when R' is —$CH_3$.

R', forming the ester portion of the sulfonated alkyl esters, is a on the average a $C_1$ to $C_8$ alkyl. Preferably, R' is on the average a $C_1$ to $C_6$ alkyl, and most preferably a $C_1$ alkyl, i.e., methyl.

When considered together, for heavy duty granular laundry detergent compositions, R and R' preferably contain a total of about 15 to 17 carbons distributed between them. Preferably the distribution is such that R is, on the average, a $C_{14}$ to $C_{16}$ alkyl (approximately a 65% $C_{14}$, 35% $C_{16}$ mix most preferably) and R' is methyl. For heavy duty liquid laundry and light duty liquid dishwashing detergent compositions, R and R' preferably contain a total of about 11 to 15 carbons, again with R' preferably being $CH_3$.

The cationic portion, M, is an alkali metal or alkaline earth metal cation or mixture thereof. Preferably, M is selected from the group consisting of sodium, potassium, lithium, magnesium and calcium, and mixtures thereof. Most preferably, M is sodium or a mixture containing sodium. When M is an alkali metal cation (valence=1) n is 1 and when M is an alkaline earth metal cation (valence=2) n is 2.

The impurities contained in the alkyl ester surfactant preferably amount to less than about 10%, more preferably less than about 5%, by weight of the surfactant. Such impurities include sulfonated fatty acid disalts, fatty acid salts, and fatty acid alkyl esters. These impurities, when present in the surfactant, decrease the desirable cleaning characteristics for detergent compositions (when compared to compositions containing the surfactant without impurities) and worsen handling difficulties during processing of the surfactant.

The sulfonated fatty acid salt impurity comprises, e.g., sulfonated fatty acid salts of the formula:

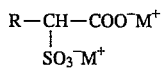

when M is a monovalent cation. This impurity is commonly referred to as disalt. R is on the average a $C_4$ to $C_{22}$ alkyl, and M is an alkali metal or alkaline earth metal cation. It is theorized, although not wishing to be bound by theory, that the the acid form of disalts (di-acids), are formed in the presence of water via hydrolysis reactions. During sulfonation processes, a portion of the fatty acid alkyl esters react with sulfur trioxide, $SO_3$, to form what is commonly called a mixed anhydride. The mixed anhydride reacts with water to form di-acids in one hydrolysis reaction. In another hydrolysis reaction, un-neutralized sulfonated alkyl esters react with water to form di-acids. These di-acids form disalts upon neutralization. Disalt may also form via a hydrolysis reaction involving sulfonated alkyl esters and water at higher pH levels. The formation of higher levels of disalts have been observed during batch-type neutralization process steps.

The fatty acid salt impurity (commonly referred to as soaps) comprises fatty acid salts of the formula $(RCH_2COO^-)_nM_{n+}$ wherein R is on the average a $C_4$ to $C_{22}$ alkyl, M is an alkali metal or alkaline earth metal cation, and n is 1 when M is an alkali metal cation and n is 2 when M is an alkaline earth metal cation. Although not wishing to be bound by theory, it is believed that soaps are formed via a hydrolysis reaction wherein un-sulfonated fatty acid alkyl esters react with water to form fatty acids. The fatty acids subsequently form soaps upon neutralization.

The fatty acid alkyl ester impurity comprise fatty acid esters of the formula $RCH_2COOR'$ wherein R is on the average a $C_4$ to $C_{22}$ alkyl and R' is on the average a $C_1$ to $C_8$ alkyl. The source of this impurity is believed to be the unreacted (unsulfonated) fatty acid alkyl esters. It is desirable to keep the level of this component as low as possible due to loss of yield, purity, performance and good in-process handleability.

Other impurities which are undesirable may exist as a component of the sulfonated fatty acid alkyl ester surfactant. In methyl ester surfactants, di-methyl sulfate ("DMS") having the formula $CH_3$—$OSO_2O$—$CH_3$ is highly undesirable as a component in the surfactant since it is a severe irritant of the eyes, respiratory tract, and skin and can be absorbed into the body through the skin. It has been observed that processes comprising a step conducted in aqueous media result in a surfactant product containing a very much reduced level of DMS. The production of DMS is more prevalent in processes conducted in non-aqueous, anhydrous media.

DMS can be produced during the sulfonation of fatty acid methyl esters. Additionally, though, higher levels of DMS have been observed when the neutralization step is conducted in a normal batch method. Very low levels of DMS impurity can be achieved by over-neutralizing the sulfonated methyl ester acid mix, i.e., neutralizing the acid mix with a stoichiometric excess of alkoxide solution to a pH of at least about 10. It has been found that DMS decomposes more quickly and completely during neutralization when the pH of the acid mix is raised to a pH above about 10.

Therefore, the process herein comprises over-neutralizing the acid mix formed by the sulfonation of fatty acid alkyl esters to a pH of at least about 10 followed by re-neutralizing the product to a pH of about 5 to 9. DMS decomposes more quickly and completely during the neutralization step when the pH of the acid mix is raised to this higher pH. The resultant product is then re-neutralized to a pH between about 5 and 9. A preferred process herein involves conducting the neutralization step C in a continuous fashion, i.e., the base and acid mixes are simultaneously fed into a reaction zone. A buffering agent may also be incorporated at the neutralizing step which provides greater ease in attaining desired pH levels.

In addition to the impurities set forth above, other impurities may be present in the neutralized paste including: sodium methyl sulfate; sodium sulfate; and color bodies. The color body impurities result from the harsh and complex sulfonation reaction required for alkyl esters, as well as minor side reactions of $SO_3$ with impurities in the alkyl ester starting material (mono-, di- or tri-glycerides for example), or unsaturation in the methyl esters. Even very small quantities of certain light-absorbing chemicals can create a dark visual appearance.

It is desirable to maintain the levels of impurities including disalt, soap, fatty acid alkyl ester and DMS impurities to a minimum when considering the production of the alkyl ester surfactant. The reduction in impurity contents in the surfactant improves the performance and formulatability of detergent compositions. The level of certain impurities, particularly DMS and disalt impurities, in the end-product is minimized by over-neutralizing the product stream of step A with an alkoxide solution prepared by combining alkoxide with a sacrificial ester in an anhydrous, i.e., alcoholic, medium, then re-neutralizing to a pH between about 5 and 9.

Starting Materials

The starting material for the process of this invention include fatty acid alkyl esters of the formula:

$$RCH_2COOR'$$

wherein R is on the average a $C_4$ to $C_{22}$ alkyl, and R' is on the average a $C_1$ to $C_8$ alkyl. Normally the alkyl chain, R, is a mixture of alkyl chains ranging in length, on the average, from about 4 carbons to 22 carbons. Preferably R is, on the average, a $C_{10}$ to $C_{16}$ alkyl, and R' is on the average a $C_1$ to $C_6$ alkyl. R' is most preferably $C_1$ (methyl) particularly when R is, on the average, a saturated $C_{14}$ to $C_{16}$ hydrocarbon. The R in the fatty acid alkyl ester starting material will correspond to the R for the sulfonated fatty acid alkyl esters in the resultant surfactant product since the fatty acid alkyl esters directly react with the reactants in steps A and C to form the sulfonated alkyl esters.

Preferably the R' in the fatty acid alkyl ester starting material is the same as the R' in the sulfonated alkyl ester. To obtain this result, the number of carbon atoms in the alcohol of step B, the alkoxide in step B, and R' of the fatty acid alkyl ester starting material are the same. Since R' is most preferably methyl, the alkoxide solution of step B is preferably formed by combining methoxide and methanol with the sacrificial ester.

The fatty acid alkyl ester starting material can be derived from unbranched $C_6-C_{24}$ carboxylic acids and $C_1-C_8$ alcohols. From an economic standpoint, the methyl esters of commercial fatty acids are preferred. Methyl esters from palm kernel oil, coconut oil or tallow oil may be used. Since, during the sulfonation step, undesirable color bodies are formed due, in part, to unsaturated chain lengths in the fatty acid alkyl ester, the original fatty acid esters should be hydrogenated to such an extent that their I.V. (iodine value) number is less than about 0.5.

Sulfur trioxide, $SO_3$, which may be used during the sulfonation step A can be derived from passing a mixture of $SO_2$ and oxygen over a heated catalyst such as platinum or vanadium pentoxide.

The alcohol contained in the alkoxide solution of step B and utilized in an optional, intermediate alcohol reaction step is preferably a linear primary aliphatic $C_1$ to $C_8$ alcohol. Methanol, the preferred alcohol, can be derived from: (a) high-pressure catalytic synthesis from carbon monoxide and hydrogen, (b) partial oxidation of natural gas hydrocarbons, (c) gasification of wood, peat, and lignite or (d) methane with molybdenum catalyst (experimental). Ethanol can be derived from: (a) ethylene by direct catalytic hydration or with ethyl sulfate as an intermediate, (b) fermentation of biomass, especially agricultural wastes, or (c) enzymatic hydrolysis of cellulose. Propyl alcohol can be derived from the oxidation of natural gas hydrocarbons, also from fusel oil. Butyl alcohol can be derived from the hydrogenation of butyraldehyde, obtained in the Oxo process or condensation of acetaldehyde to form crotonaldehyde, which is then hydrogenated (aldol condensation). Other alcohols can be derived from the hydrogenation of fatty acids.

The alkoxide solution utilized in step B comprises: an alkoxide of the formula $(RO^-)_nM_{n+}$ wherein n is 1 when M is an alkali metal cation and n is 2 when M is an alkaline earth metal cation; a $C_1$ to $C_8$ alcohol; and a low level of water. The alkoxide solution can be derived by dissolving a metal (corresponding to the M in the alkoxide) in an alcohol. Solutions containing the desired alkoxide and alcohol are also commercially available, e.g., 25% concentration methoxide in methanol solution commercially available from Occidental Chemical. Alternatively, the alkoxide can be derived by chemically reacting an alcohol with a 50% hydroxide solution in a column, continuously removing alkoxide in alcohol solution at the bottom and dilute alcohol/water solution from the top of the column. See U.S. Pat. No. 2,877,274 (Kramis). Since the process herein requires that the alkoxide solution contain a low level of water and ultimately requires reaction conditions that are substantially anhydrous, a major portion of water is preferably removed from the solution prior to use in the process. Also, the alkoxide solution is preferably not derived by dissolving, e.g., sodium or potassium hydroxide in an alcohol. Such reactions yield one mole of water for every mole of alkoxide produced.

In the instant process, the solution of step B also requires a sacrificial ester at a level corresponding to molar ratios of sacrificial ester to water between about 0.5:1 to about 2:1, preferably between about 0.75:1 and 1.5:1. This small level of sacrificial ester reacts with water present in the alkoxide solution of step B to form an alcohol and an acid thereby forming an alkoxide solution that is substantially anhydrous. In step C, this prevents or inhibits the formation of undesirable impurities like disalts during the over-neutralization of the product of step A, i.e., acid mix, with the alkoxide solution.

Theoretically, the product of step A ("acid mix") could be neutralized in a totally anhydrous medium of a $C_1-C_8$ alcohol to result in neutralized alkyl ester surfactant product. In practice, though, such anhydrous conditions are economically and feasibly impractical. Commercially available alkoxide solutions may contain as much as 0.5% water or more. Moreover, when alcoholic solutions like the alkoxide solution of the invention herein are exposed to ambient conditions, they will pick up water from the atmosphere and will result in additional water in solution. Water present in the reaction mixture of step C will react with certain species therein via hydrolysis reactions to produce undesirable impurities. The combining of a sacrificial ester with the alkoxide solution substantially eliminates water in the alkoxide solution and helps prevent these undesirable hydrolysis reactions from occurring and reduces the level of undesirable impurities in the resultant surfactant product.

Any compatible material or mixture of materials which will react with water in alcoholic media can be utilized as the sacrificial ester in the instant invention. For the purposes intended in the invention herein, the sacrificial ester has the formula:

$$R^1COOR^2$$

wherein $R^1$ is a $C_1$ to $C_4$ alkyl or benzoate and $R^2$ is a $C_1$ to $C_8$ alkyl.

Preferably $R^1$ is $CH_3$ or benzoate and $R^2$ is $CH_3$. Examples of preferred materials which can be used either alone or in combination as the sacrificial ester herein include methyl acetate and methyl benzoate. Most preferably the sacrificial ester is selected from the group consisting of methyl acetate and mixtures containing methyl acetate.

The Process

Numerous descriptions of processes for the manufacture of the sulfonated fatty acid alkyl ester surfactants are disclosed in the technical literature. The process of this invention herein comprises four essential steps:

A. sulfonating fatty acid alkyl esters,

B. combining an alkoxide solution with a sacrificial ester to form a substantially anhydrous alkoxide solution;

C. over-neutralizing with the substantially anhydrous alkoxide solution to a pH of at least about 10; and D. re-neutralizing in a substantially anhydrous medium to a pH between about 5 and 9.

This process results in a high purity sulfonated fatty acid alkyl ester surfactant. The resultant product solution may be subjected to a color-body removal process before the surfactant is incorporated into a detergent composition.

Sulfonation of Fatty Acid Alkyl Esters

The sulfonation of the fatty acid alkyl esters carried out in step A of this invention can be carried out by any known sulfonation process. For example, alkyl esters of $C_8$–$C_{20}$ carboxylic acids can be sulfonated with gaseous $SO_3$ in a falling film reactor. The alkyl esters and gaseous $SO_3$ will not completely react to form sulfonated fatty acid alkyl esters at ambient temperatures and pressures. Therefore, this sulfonation process generally includes a mixing step wherein the alkyl esters are brought into contact with a $SO_3$/air mixture (about 5% $SO_3$ in air, by volume) at a molar ratio of $SO_3$:alkyl ester of about 1.1:1 to 1.4:1 followed by heating of the mixture to about 75°–95° C. for approximately 20–90 minutes. Preferably, the dew point of the air used for mixing with the $SO_3$ is about −40° C. or lower.

Descriptions of acceptable sulfonation processes are described in "α-Sulfonated Fatty Acids and Esters: Manufacturing Process, Properties, and Applications" by W. Stein and H. Baumann, *The Journal of the American Oil Chemists Society*, Volume 52 (1975), pp 323–325; and U.S. Pat. No. 3,485,856 incorporated herein by reference. See also *Surfactants in Consumer Products*, J. Falbe (Editor), pp. 75–80.

The fatty acid alkyl ester starting material should contain a minimum amount of unsaturated carbon double bonds, i.e., hydrogenated to such an extent that their I.V. number is less than about 0.5. During this sulfonating step, color bodies are produced due to the harsh reaction conditions (highly acidic $SO_3$, high temperature, etc.). The color quality of the product of step A is typically poor. Preferably, this product is not subjected to any intermediate process step that proceeds in aqueous media, e.g., bleaching. Hydrolysis reactions with intermediate reactants produce the acid form of sulfonated fatty acids which, upon neutralization form the disalt impurity.

It is believed, although not wishing to be bound by theory, that the reaction between the alkyl esters and $SO_3$ in step A occurs in two stages. First, $SO_3$ reacts with the alkyl ester forming an intermediate complex and activating the carbon at the alpha position (*) as follows:

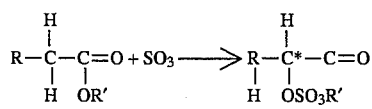

In the second stage, another molecule of $SO_3$ attaches to the activated alpha carbon (*) generating what is commonly referred to as a mixed anhydride:

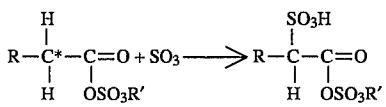

The reaction is best carried out in a falling-film reactor using very dilute $SO_3$ in an inert gas (e.g., 5% $SO_3$ in dry air, by volume). The reaction should be carried out with not more than about 40% excess $SO_3$ to avoid charring. A significant amount of unreacted fatty acid alkyl ester remains in the product stream leaving the falling film reactor. Therefore, the sulfonating step preferably includes an additional process step wherein the $SO_3$/alkyl ester mix is allowed to react at elevated temperatures (80° to 90° C.), commonly referred to as digestion. Upon heating in the digestion step, most of the mixed anhydride reacts with fatty acid alkyl esters to form the acid form of sulfonated fatty acid alkyl esters.

Formation of a Substantially Anhydrous Alkoxide Solution

The formation of the alkoxide solution herein can be carried out by any known means for mixing ingredients. The only requirement for purposes of step B of the process herein is that a substantially anhydrous alkoxide solution be formed. The components of step B comprise (i) an alkoxide solution comprising an alkoxide of the formula $(RO^-)_n M_{n+}$; a $C_1$ to $C_8$ alcohol; and no more than about 1% water, by weight of the alkoxide solution, and (ii) a sacrificial ester of the formula $R^1 COOR^2$. These are combined to form a substantially anhydrous alkoxide solution. The molar ratio of sacrificial ester to water is from about 0.5:1 to about 2:1, preferably from about 0.75:1 to about 1.5:1.

During this process step, water present in the mixture of step B reacts with the sacrificial ester to form an acid and alcohol in accordance with the general equation:

$$R^1 COOR^2 + H_2O \xrightarrow{\text{alkoxide/alcohol}} R^1 COOM + R^2 OH \quad (I)$$

The method by which the alkoxide solution is formed must provide for the intimate mixing of the reactants in the reaction vessel and includes, e.g., mixing the ingredients with a paddle blade mixer. Since the reaction is taking place in an alcoholic medium, the mixing apparatus need not be elaborate or costly; the mixture is relatively free-flowing.

The process step B may involve combining the alkoxide and alcohol prior to mixing in the sacrificial ester or may comprise mixing the sacrificial ester into an alkoxide in alcohol solution described above (see starting materials). Preferably, step B consists of mixing the sacrificial ester into a methoxide/methanol solution containing no more than about 1% by weight water wherein the molar ratio of sacrificial ester to water is from about 0.5:1 to about 2:1, most preferably from about 0.75:1 to about 1.5:1. The resultant methoxide solution is substantially anhydrous and is used to neutralize the acid mix of step A.

Over-neutralization of a pH of at least about 10

The product of step A is substantially all in the acid form of sulfonated fatty acid alkyl esters. In accordance with step C of the process herein, this acid mix is neutralized to a pH of at least about 10 with the substantially anhydrous alkoxide solution of step B.

The primary reaction taking place during step C (when n for the alkoxide is 1) is:

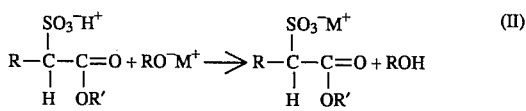

The amount of alkoxide solution required for Reaction (II) is considered to be within the experimental ability of one having ordinary skill in the art. The amount of alkoxide present in the alkoxide solution utilized in step C is generally the amount required to neutralize the product of step A to a pH of at least about 10.

An undesirable side reaction of process step A produces the highly undesirable dimethyl sulfate (DMS) impurity. In processes comprising a step conducted in aqueous media, e.g., aqueous bleaching step, DMS is not a significant problem because DMS readily degrades in aqueous media. However, when the process is conducted in substantially anhydrous media, as in the process of the invention herein, DMS impurity is particularly troublesome. In anhydrous media, the DMS impurity does not readily degrade unless special precautions or process variations are incorporated. To eliminate the DMS impurity which would otherwise remain in the surfactant, the process herein (conducted in substantially anhydrous conditions) comprises over-neutralizing the acid mix of step A to a pH of at least about 10. It has been found that the DMS impurity is readily degraded (more completely and quickly) at this higher pH range in non-aqueous media.

In addition to Reaction II above, other reactions may take place during step C, but these are for the most part undesirable. At higher pH levels, certain hydrolysis reactions may occur which result in the formation of undesirable disalt impurity if water is present. The hydrolysis reaction of most concern involves the hydrolysis of neutralized sulfonated fatty acid alkyl esters. Under this reaction, the species reacts with water to form undesirable disalt impurity. The hydrolysis reaction is particularly troublesome because process step C is conducted at a final pH of at least about 10. The hydrolysis reaction heavily favors formation of the disalt impurity at these high pH levels, i.e., pH levels above about 10. At lower pH levels, i.e., pH levels of about 7, the hydrolysis reaction does not pose a serious detriment.

The dilemma encountered herein involves attempting to eliminate or reduce the amount of DMS impurity while attempting to inhibit or prevent the formation of disalt impurity. In order to eliminate the DMS impurity the process comprises elevating the pH of the reaction mixture in step C to at least about 10. Yet, at this higher pH range, the reaction mixture favors certain hydrolysis reactions which produce undesirable disalt impurity. Therefore, when conducting the neutralization reactions of the invention herein, care should be taken to conduct such reactions in substantially anhydrous media with components that are substantially anhydrous. By neutralizing the acid mix with the substantially anhydrous alkoxide solution to a pH level of at least about 10, DMS impurity is allowed to degrade while the formation of disalt impurity is inhibited and, therefore, a high purity sulfonated fatty acid alkyl ester surfactant is produced which contains low levels of disalt and DMS impurities.

In a preferred batch process, the alkoxide solution contains a buffering agent which facilitates maintaining the pH of the neutralized product of step D within the desired pH range. It is in the final pH range of about 5 to 9 that optimum performance and chemical stability of the resultant surfactant are realized. Targeting the pH of the neutralized reaction product of step C to between about 5 and about 9, preferably between about 6 and about 8, minimizes undesirable degradation or hydrolysis of the resultant surfactant.

The buffering agent is generally present in the alkoxide solution at a level such that the molar ratio of the alkoxide to buffering agent is from about 5:1 to about 100:1, preferably from about 10:1 to about 50:1. Any compatible material or mixture of materials which has the effect of maintaining the pH within the pH range of about 5 to about 9 can be utilized as the buffering agent in the instant invention. Such materials have a pKa value between about 5 and 9, preferably between about 6 and 8. The buffering agent can include, for example, citric acid, succinic acid, phosphoric acid, and pyrophosphoric acid.

Such materials can be used either alone or in combination as the buffering agent. Preferably, the buffering agent is selected from the group consisting of citric acid and mixtures containing citric acid.

This preferred batch process provides an improved method for neutralizing the acid form of sulfonated alkyl esters. Without a buffering agent, targeting a particular reaction mixture to a desired pH can be difficult to perform. Under typical neutralization processes which do not incorporate a buffering agent, the exact stoichiometric equivalent of alkoxide relative to acid mix is determined. Then during neutralization, the pH must be continually monitored to avoid over- or under-neutralization of the acid mix. Even so, over- or under-neutralization of the acid mix is common. With the addition of a buffering agent, such batch neutralization is accomplished more easily and more accurately to the desired pH. One can estimate the quantity of alkoxide required to neutralize the acid mix, then perform the neutralization to the desired pH level without excessive monitoring of the pH level of the reaction mixture.

Additionally, some excess amount of buffering agent may remain in the finished surfactant product which will serve as a hydrolysis inhibitor. Dry surfactant powder can absorb water from the atmosphere, particularly in humid climates. Such water may react with the sulfonated alkyl esters according to certain hydrolysis reactions to produce disalt impurity. The buffering agent herein inhibits such reactions and provides a chemical stability to the surfactant product.

As used herein, the term "substantially anhydrous" requires that the level of water in a solution or mixture be less than about 0.1% by weight of the solution or mixture. Preferably the solution or mixture contains less than about 0.05% by weight of water. Most preferably, the solution or mixture is essentially water-free. A specific advantage in conducting the process of the invention herein via substantially anhydrous media is the ease of processability of the reactant and product solutions. The technical literature recognizes the problems encountered with sulfonated fatty acid alkyl ester surfactant solutions containing water. It seems that the alkyl ester surfactant forms viscous pastes in water which can require special handling equipment, e.g., special pumps, heat exchangers, etc. An advantage of conducting the process of the invention herein via anhydrous alcoholic media is that the process does not require the special equipment that may be required for processes involving an aqueous media. The process of the invention herein involves solutions which are relatively fluid and non-viscous which do not require special pumps to process. These advantages are in addition to inhibiting or preventing the formation of the disalt and other impurities. Moreover, the substantially anhydrous alcoholic medium allows for the effective separation of dark colored impurities during post-neutralization purification steps, i.e., a no-bleach color-body removal process described below.

As used herein, the term "neutralize" means batch or continuous neutralization. Continuous neutralization requires mixing the reactants simultaneously at essentially equimolar ratios in such a manner that intimate mixing of the reactants with vigorous agitation is achieved. It has been observed that normal batch neutralization, wherein an alkoxide solution is added into an acid mix containing the acid form of sulfonated fatty acid methyl esters, initially produces undesirable levels of DMS (dimethyl sulfate) impurity. Since the process herein comprises raising the pH level to at least about 10 where the DMS impurity readily degrades, reverse batch neutralization is preferred. Continuous neutralization, wherein an acid mix containing the acid form of sulfonated fatty acid alkyl esters and an alkoxide solution are simultaneously fed into a reaction chamber with vigorous agitation, maximizes yield of the surfactant and minimizes impurities including DMS. Sufficient agitation and/or mixing should be provided to allow the reactants to intimately mix and completely react in the chamber. It has been found that a wide range of mixers provide adequate mixing. For example, high shear mixers commercially available from Charles Ross & Son Company, Greerco Company or IKA as well as static motionless mixers (providing shear rates as low as about 5000 sec$^{-1}$) provide the required conditions for continuous neutralization of the reactants.

Because the process of the invention herein is conducted in non-aqueous media, i.e., substantially anhydrous alcoholic media, the reactant and product streams exhibit good handling and in-process flow properties. In aqueous media, sulfonated fatty acid alkyl ester surfactants form viscous pastes which are difficult to process. In anhydrous media of a $C_1$ to $C_8$ alcohol, these surfactants are fluid and do not require sophisticated or expensive designs or equipment to process.

The term "pH" as referred to in the process of the invention hereof is defined as the pH measured from a 1–2% (by weight of the surfactant) solution of the product of step C or step D in deionized water with a pH meter.

Re-neutralization to a pH of about 5 to 9

The product of step C is at a pH level which is undesirable for most purposes. Therefore, the product of step C is neutralized to a pH of about 5 to about 9. Any known method for neutralizing a basic solution to a substantially neutral pH may be used.

Particularly preferred methods include neutralizing the product of step C with an anhydrous solution of a weak acid having a pKa between about 5 and 9, e.g., citric acid. Any method involving the use of aqueous solutions of, e.g., HCl or $H_2SO_4$, is not preferred. Such methods involve water which favor undesirable hydrolysis reactions. This process step should also not consist of re-neutralizing the product of step C with additional acid mix of step A. This method brings in additional undesirable DMS impurity.

The amount of the neutralizing component required for the reaction taking place in step D is considered to be within the experimental ability of one having ordinary skill in the art. The amount of the component used to neutralize the product of step C is generally the amount required to neutralize the product of step C to a pH of about 5 to 9.

Optional Process Step

Preferably, the process of the invention herein should not include any process step wherein bleaching of the reactants is conducted. Such bleaching steps are described in, e.g., U.S. Pat. Nos. 4,695,409 and 4,820,451 which cite references describing acidic bleaching with hydrogen peroxide (U.S. Pat. Nos. 3,142,691; 3,159,547; 3,251,868; and 3,354,187) and hypochlorite (U.S. Pat. No. 3,452,064). Such bleaching steps are generally conducted in aqueous media and would raise the problems discussed above regarding impurities and in-process flow properties. Therefore, the process of the invention preferably does not include any bleaching process step, whether intermediate or in combination with the process steps.

Even though the product of step A is substantially all in the acid form of sulfonated fatty acid alkyl esters, a significant amount of the mixed anhydride may remain in the reaction mixture after the sulfonation step A. The mixed anhydrides, if allowed to react with water, will form sulfonated fatty acids via a hydrolysis reaction. Upon neutralization, these fatty acids form the disalt impurity. It is desirable, therefore, to convert the mixed anhydrides remaining in the product stream of step A to the acid form of sulfonated fatty acid alkyl esters. This is accomplished by reacting the mixed anhydrides with an alcohol.

Thus, an optional, but preferred, intermediate step involves the reaction of the sulfonated product of step A with an alcohol. The alcohol reaction step comprises reacting the product of step A and from about 3% to 25%, preferably about 10% to 20%, by weight of the product of step A, of an alcohol. The alcohol is a $C_1$ to $C_8$ alcohol, preferably a $C_1$ to $C_6$ alcohol, most preferably methanol particularly when the fatty acid alkyl ester starting materials are $C_{14}$–$C_{16}$ fatty acid methyl esters. In processes for making methyl ester sulfonates, DMS impurity will be produced at a more noticeable rate when such process involves a methanol reaction step. This is because the excess $SO_3$ and substantially anhydrous methanol medium favors the production of DMS. However, the process of the invention herein is particularly suited for handling this increased level of DMS as described hereinbefore. Reacting the product of step A with a $C_1$ to $C_8$ alcohol and subsequently neutralizing this product with the alkoxide solution in accordance with the process of the invention herein produces a high purity sulfonated fatty acid alkyl ester surfactant.

During this alcohol reaction step, the anhydride reacts with the alcohol to generate more desired product for neutralization in step C below, i.e., the acid form of the sulfonated fatty acid alkyl ester, according to the following reaction:

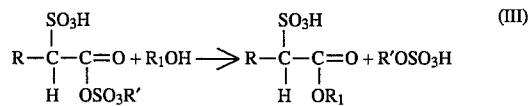
(III)

This reaction is relatively fast and most of the remaining mixed anhydrides are converted to the acid form of sulfonated fatty acid alkyl esters when the appropriate level of alcohol is used.

Therefore, a preferred embodiment of the invention herein pertains to a process for preparing the preferred sulfonated fatty acid methyl ester surfactant. Such process comprises:

A. sulfonating fatty acid methyl esters of the formula:

$RCH_2COOCH_3$ wherein R is on the average a $C_{10}$ to $C_{16}$ alkyl;

B. reacting the product of step A with from about 5% to 25%, by weight of the product of step A, of a $C_1$ to $C_6$ alcohol, preferably methanol; and C. combining a methoxide solution comprising:
   i) a methoxide of the formula $(CH_3O^-)_n M^{n+}$ wherein M is an alkali metal or alkaline earth metal cation, and n is 1 when M is an alkali metal cation and n is 2 when M is an alkaline earth metal cation;

ii) methanol; and iii) no more than about 1% water, by weight of the solution;

with a sacrificial ester of the formula $R^1COOR^2$ wherein $R^1$ is a $C_1$ to $C_4$ alkyl or benzoate and $R^2$ is a $C_1$ to $C_8$ alkyl; wherein the molar ratio of the sacrificial ester to water is from about 0.5:1 to about 2:1;

D. over-neutralizing the product of step A to a pH of at least about 10 with the methoxide solution; and E. re-neutralizing the product of step D in a substantially anhydrous medium to a pH of about 5 to 9.

This process results in high-purity, high-yield surfactant solution containing sulfonated fatty acid methyl esters and low levels of impurities including disalts, soaps, fatty acid methyl esters and DMS.

The resultant product of the process herein is an essentially non-aqueous mixture comprising sulfonated fatty acid alkyl ester surfactant and alcohol. This product may be subjected to a working-up procedure depending on the end use desired. For example, simple separation of the resultant components can be accomplished in many ways including precipitation of the surfactant from the solution, evaporation of the alcohol or a combination thereof. The known processes for sulfonating fatty acid alkyl esters in accordance with step A of the invention will likely suffer from the formation of dark-colored impurities. In order to obtain high sulfonation yields, excess sulfonating agent in combination with greater processing times and/or temperatures is required. These conditions can result in undesirable side reactions including the formation of dark-colored impurities.

For aesthetic and other reasons, the dark-colored sulfonated fatty acid alkyl ester compositions are not suitable for use directly in washing or cleansing agents in detergent products. The dark-colored impurities can be separated from the solution comprising the sulfonated fatty acid alkyl ester surfactant and a suitable solvent, e.g., a $C_1$–$C_8$ alcohol, by separation methods described hereinafter. Separation of the dark-colored impurities from the solution can be enhanced with an adsorbent material. After removal of the dark colored impurities, the sulfonated fatty acid alkyl ester surfactant can be recovered from the solvent to yield a product with improved, i.e. lighter, color.

In particular, a process for improving the color of the surfactant (containing dark-colored impurities formed during the preparation of the surfactant) comprises:

(1) forming a solution comprising:

(a) the sulfonated fatty acid alkyl ester surfactant and dark-colored impurities formed during the preparation of the surfactant; and (b) a solvent in an amount sufficient to substantially dissolve the surfactant;

(2) separating said dark-colored impurities from the solution;

(3) recovering surfactant from the solution.

The step comprising separating dark-colored impurities from the solution of the surfactant in alcohol can be achieved by settling/clarification, centrifugation, filtration, adsorption, or a combination thereof. In a preferred embodiment, the solution is treated with an adsorbent material such as activated carbon, activated alumina, or silica gel.

After separation of the dark-colored impurities from the solution, the surfactant having improved color can be recovered from the solvent solution by known methods. Such recovery methods include, e.g., precipitation of the sulfonated fatty acid alkyl ester from the solution, evaporation of the lower alcohol solvent from the solution or a combination thereof.

The process for making sulfonated fatty acid alkyl ester surfactant of the invention hereof is particularly suited to the process for improving the color of the surfactant since the surfactant is already substantially dissolved in a solvent ($C_1$–$C_8$ alcohol). In order to improve the color thereof, one simply needs to separate the dark-colored bodies from the solution and recover the surfactant from the solvent. Having subjected the surfactant to the process for improving the color thereof, i.e., steps (1)–(3) above, the resultant product can be used directly in cleansing and washing agents and products.

As used herein, all percentages, parts, and ratios are by weight unless otherwise stated.

The following examples illustrate the processes of the invention and facilitate its understanding.

EXAMPLE I

Ester sulfonic acid is produced by conventional sulfonation of palm stearin fatty acid methyl ester. The acid component of the methyl ester consists essentially of saturated fatty acids with an Iodine Value of 0.28 and the following chain length distribution (by weight percent):

|  |  |
|---|---|
| $C_{12}$ | 0.23 |
| $C_{14}$ | 1.55 |
| $C_{15}$ | 0.08 |
| $C_{16}$ | 66.75 |
| $C_{17}$ | 0.15 |
| $C_{18}$ | 31.28 |
| $C_{20}$ | 0.19 |

The sulfonation reaction is carried out at 80° C. to 95° C. in an annular falling film reactor using a mixture of sulfur trioxide and air ($SO_3$ content: 3–4% by volume; $SO_3$ excess: 15–30 mole percent). The sulfonated methyl ester acid mix is then digested in the presence of an added 25 parts of $CH_3OH$ in a closed vessel for 35 to 40 minutes at a temperature of 80° C. to 95° C. The degree of sulfonation after digestion is 95%.

A substantially anhydrous solution (essentially water-free) of sodium methoxide in methanol is prepared by mixing 99 weight % of a commercially available methoxide in methanol solution (from Occidental Chemical; concentration=25% wt % methoxide in methanol; containing 0.2 wt % water) with 1 weight % methyl acetate in a standard paddle blade mixer for 5 minutes.

The acid mix is then neutralized in a paddle blade mixer by adding sufficient anhydrous methoxide solution to the acid mix to raise the pH of the neutralized acid mix to 10.5. The resulting solution is maintained at this pH level for about 60 minutes. The solution is then neutralized in the mixer to a pH of 7.0 using granular anhydrous citric acid.

The methyl ester sulfonate surfactant is isolated from the methanol solution by chilling the solution to 5° C. and filtering off the precipitated surfactant. After drying the Wet powder, the resultant surfactant is shown to contain no detectable DMS level and low level of disalt impurity. Such surfactant demonstrates lower levels of impurities than similar surfactants prepared via other processes including processes conducted in aqueous media.

What is claimed is:

1. A process for preparing a sulfonated fatty acid alkyl ester surfactant comprising from about 80% to about 100%, by weight, of a sulfonated fatty acid alkyl ester of the formula:

$$[RCH(SO_3^-)COOR']_n M^{n+}$$

wherein R is a $C_4$ to $C_{22}$ alkyl, R' is a $C_1$ to $C_8$ alkyl, M is an alkali metal or alkaline earth metal cation, n is 1 when M is an alkali metal cation, and n is 2 when M is an alkaline earth metal cation, said process comprising:

A. sulfonating fatty acid alkyl esters having the formula $RCH_2COOR'$ wherein R is a $C_4$ to $C_{22}$ alkyl and R' is a $C_1$ to $C_8$ alkyl;

B. combining an alkoxide solution containing no more than about 1% by weight water with a sacrificial ester of the formula $R^1COOR^2$ wherein $R^1$ is a $C_1$ to $C_4$ alkyl or benzoate and $R^2$ is a $C_1$ to $C_8$ alkyl to form a substantially anhydrous alkoxide solution; wherein the molar ratio of sacrificial ester to water is from about 0.5:1 to about 2.0:1;

C. over-neutralizing the product of step A to a pH of at least about 10 with the substantially anhydrous alkoxide solution of step B; and D. re-neutralizing the product of step C in a substantially anhydrous medium to a pH of about 5 to 9.

2. A process for preparing a sulfonated fatty acid alkyl ester surfactant according to claim 1, wherein the alkoxide solution consists essentially of sodium methoxide, methanol and no more than about 1% by weight water.

3. A process according to claim 1 wherein the sacrificial ester is selected from the group consisting of methyl acetate, methyl benzoate and mixtures thereof.

4. A process according to claim 2 wherein the sacrificial ester is selected from the group consisting of methyl acetate, methyl benzoate and mixtures thereof.

5. A process according to claim 1 wherein the molar ratio of sacrificial ester to water is from about 0.75:1 to about 1.5:1.

6. A process according to claim 2 wherein the molar ratio of sacrificial ester to water is from about 0.75:1 to about 1.5:1.

7. A process according to claim 4 wherein the molar ratio of sacrificial ester to water is from about 0.75:1 to about 1.5:1.

8. A process according to claim 1 wherein the substantially anhydrous alkoxide solution is essentially water-free.

9. A process according to claim 7 wherein the substantially anhydrous alkoxide solution is essentially water-free.

10. A process according to claim 1 further comprising reacting the product of step A with from about 3 to 25% by weight of an alcohol prior to conducting step C.

* * * * *